(12) United States Patent
Ozaki

(10) Patent No.: US 6,626,644 B2
(45) Date of Patent: Sep. 30, 2003

(54) MAGNETICALLY LEVITATED PUMP AND CONTROLLING CIRCUIT

(75) Inventor: Takayoshi Ozaki, Iwata (JP)

(73) Assignees: NTN Corporation, Osaka (JP); Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/983,368

(22) Filed: Oct. 24, 2001

(65) Prior Publication Data

US 2002/0051711 A1 May 2, 2002

(30) Foreign Application Priority Data

Oct. 30, 2000 (JP) ........................................ 2000-330409
Dec. 11, 2000 (JP) ........................................ 2000-375512
Dec. 11, 2000 (JP) ........................................ 2000-375934

(51) Int. Cl.[7] ................................................ F04B 49/06
(52) U.S. Cl. ..................... 417/45; 417/44.1; 417/423.7; 415/900
(58) Field of Search ................................. 417/45, 423.4, 417/423.7, 423.12, 44.1, 44.3, 44.11, 410.1, 420; 415/98, 900, 101, 103

(56) References Cited

U.S. PATENT DOCUMENTS

| | | | | |
|---|---|---|---|---|
| 4,944,748 A | * | 7/1990 | Bramm et al. ................. 623/3 |
| 5,112,202 A | * | 5/1992 | Oshima et al. ........... 417/423.7 |
| 5,332,374 A | * | 7/1994 | Kricker et al. ............... 417/420 |
| 5,686,772 A | * | 11/1997 | Delamare et al. ........... 310/90.5 |
| 5,725,357 A | * | 3/1998 | Nakazeki et al. .............. 417/18 |
| 5,961,291 A | * | 10/1999 | Sakagami et al. ............. 417/42 |
| 6,071,093 A | * | 6/2000 | Hart ........................ 417/424.2 |

FOREIGN PATENT DOCUMENTS

| | | | |
|---|---|---|---|
| JP | 09-206373 A | * | 8/1997 |
| JP | 11-244377 A | * | 9/1999 |

* cited by examiner

*Primary Examiner*—Charles G. Freay
*Assistant Examiner*—Han L Liu
(74) *Attorney, Agent, or Firm*—McDermott, Will & Emery

(57) ABSTRACT

An impeller has one surface with a soft magnetic member arranged closer to an inner diameter thereof, opposite an electromagnet, the impeller is provided with a permanent magnet arranged closer to an outer diameter thereof, opposite a permanent magnet of a rotor, and the impeller has the other surface provided with a ferromagnetic body, opposite a permanent magnet of a casing, thereby magnetically levitating the impeller, and allowing a motor stator to rotate a motor rotor to rotate the impeller.

23 Claims, 17 Drawing Sheets

MAGNITUDE OF DISTURBANCE

DISTURBANCE

VOLTAGE

A

VOLTAGE

B

VOLTAGE

C

VOLTAGE

D

DISTURBANCE

A

B

C

D

MAGNITUDE OF DISTURBANCE

DISTURBANCE

VOLTAGE

A

VOLTAGE

B

VOLTAGE

C

VOLTAGE

D

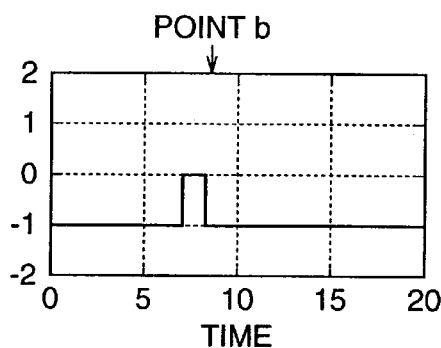
FIG. 14A  MAGNITUDE OF DISTURBANCE   DISTURBANCE
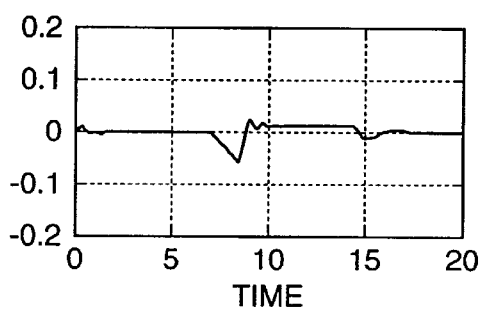
FIG. 14B  VOLTAGE   A
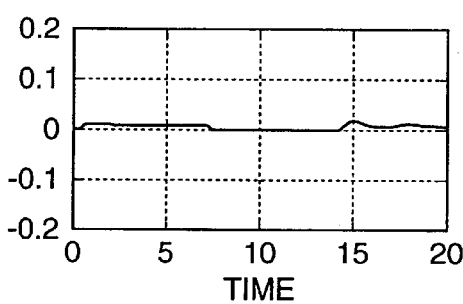
FIG. 14C  VOLTAGE   B
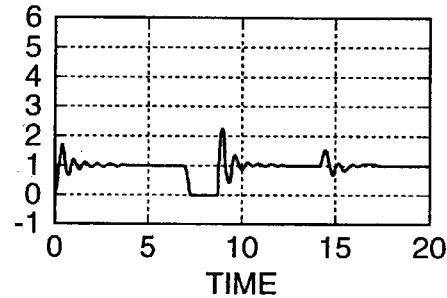
FIG. 14D  VOLTAGE   C
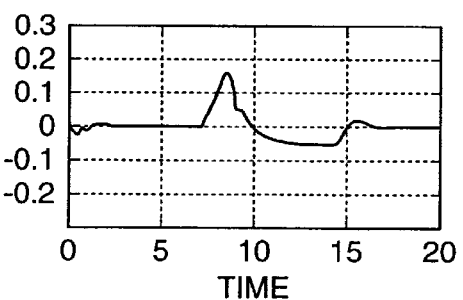
FIG. 14E  VOLTAGE   D

MAGNETICALLY LEVITATED PUMP AND CONTROLLING CIRCUIT

BACKGROUND OF THE INVENTION

1. Field of the Invention

The present invention relates generally to magnetically levitated (maglev) pumps and controlling circuits, and more specifically to clean pumps employing a magnetic bearing, such as maglev pumps for use in artificial hearts and other similar medical equipment, and controlling circuits.

2. Description of the Background Art

FIGS. 16A and 16B show a conventional maglev pump. More specifically, FIG. 16A is a vertical cross section thereof and FIG. 16B is a cross section thereof taken along a line XVIB—XVIB.

A shown in FIG. 16A, the maglev pump 1 is configured by a motor unit 10, a pump unit 20 and a magnetic bearing unit 30. In pump unit 20 internal to a casing 21 a pump chamber 22 is provided and therein an impeller 23 rotates. As shown in FIG. 16B, impeller 23 has a plurality of vanes 27 formed spirally.

Casing 21 is formed of a non-magnetic member and impeller 23 includes a non-magnetic member 25 having a permanent magnet 24 constituting a non-controlled magnetic bearing, and a soft magnetic member 26 corresponding to a rotor of a controlled magnetic bearing. Permanent magnet 24 is divided in a direction of a circumference of impeller 23 and adjacent magnets are magnetized to have opposite magnetic poles. Opposite to that side of impeller 23 having permanent magnet 24, a rotor 12 is provided external to pump chamber 22, supported by a bearing 17.

Rotor 12 is driven by a motor 13 to rotate. Rotor 12 is provided with the same number of permanent magnets 14 as permanent magnets 24 of impeller 23 to face permanent magnets 24 and also create attractive force. Adjacent permanent magnets 14 are also magnetized to have opposite magnetic poles.

Opposite that side of impeller 23 having soft magnetic member 26, at least three electromagnets 31 and at least three positional sensors 32 are provided circumferentially in magnetic bearing unit 30 to attain balance with the attractive force of permanent magnets 24 and 14 in pump chamber 22 to maintain impeller 23 at a center of casing 21. Electromagnet 31 has a geometry of the letter C and position sensor 32 is a magnetic sensor.

In maglev pump 1 thus configured an attractive force acts axially between permanent 14 buried in rotor 12 and permanent magnet 24 provided to impeller 23. This attractive force contributes to magnetic-coupling, which rotatably drives impeller 23 and also provides radial supporting stiffness. To achieve balance with the attractive force, C-shaped electromagnet 31 has a coil passing electric current to levitate impeller 23.

When rotor 12 is rotated by a driving force provided by motor 13 formed by motor rotor 15 and motor stator 16, permanent magnets 14 and 24 form magnetic-coupling and impeller 23 thus rotates to suck a fluid through a suction port 60 and discharge the fluid through an outlet 70. Since impeller 23 is isolated from rotor 12 by casing 21 and is also not contaminated by electromagnet 31, maglev pump 1 discharges a fluid (blood if the pump is used for blood pump) maintained clean.

FIG. 17 shows the FIGS. 16A and 16B maglev pump and a circuit controlling the same. In FIG. 17, a maglev pump 200 is shown in a perspective view, at seen at a suction port 60 shown in FIG. 16A, and an axis of rotation of impeller 23 is surrounded by three electromagnets M1–M3 and three sensors S1–S3. Sensors S1–S3 provides their respective outputs which are inputs to sensor amplifiers H1–H3, respectively, amplified thereby and thus output to an operation circuit 202.

Operation circuit 202 performs an operation on sensor outputs amplified by sensor amplifiers H1–H3 and outputs to a phase compensation circuit 203 a voltage a proportional to a gap between electromagnet M1 and impeller 23, a voltage b proportional to a gap between electromagnet M2 and impeller 23, and a voltage c proportional to a gap between electromagnet M3 and impeller 23.

Phase compensation circuit 203 includes proportional plus derivative circuits PD1–PD3 and integral circuits I1–I3. Proportional plus derivative circuit PD1 and integral circuit I1 receive control voltage a. Proportional plus derivative circuit PD2 and integral circuit I2 receive control voltage b. Proportional plus derivative circuit PD3 and integral circuit I3 receive control voltage c. An output of proportional plus derivative circuit PD1 and that of integral circuit I1 are added together and thus output to a limit circuit LM1. An output of proportional and derivative circuit PD2 and that of integral circuit I2 are added together and thus output to a limit circuit LM2. An output of proportional plus derivative circuit PD3 and that of integral circuit I3 are added together and thus output to a limit circuit LM3. If limit circuits LM1–LM3 receive a signal of positive voltage they pass the signal and if they receive a signal of negative voltage then they compulsorily set the signal to be 0V. Limit circuits LM1–LM3 have their respective output signals input to power amplifiers A1–A3, respectively. Power amplifiers A1–A3 amplify the output signals, respectively, to drive their respective electromagnets M1–M3. Thus the control circuits allow an operation to be performed based on the outputs of sensors S1–S3 individually for electromagnets M1–M3 to drive electromagnets M1–M3.

FIG. 18 is a block diagram showing another example of the circuit controlling the maglev pump. The FIG. 17 control circuit includes phase compensation circuit 203 having proportional plus derivative circuits PD1–PD3 and integral circuits I1–I3 independently provided for electromagnets M1–M3, whereas the FIG. 18 control circuit, does not have an independent phase compensation circuit for each electromagnet. More specifically, it is provided with a phase compensation circuit for each mode of movement of an impeller controlled by a magnetic bearing. Herein, impeller 23 has separate modes of movement including a translative movement in the direction of an axis of translative movement of the impeller, and rotative movements around the axis of translative movement of the impeller, orthogonal to each other relative to the axis, i.e., a pitching movement and a yawing movement.

With reference to FIG. 18, separation circuit 204 performs an operation on sensor signals output from sensor amplifiers H1–H3 and outputs the impeller 23 translative movement parameter z, pitching movement parameter θx and yawing movement parameter θy. Phase compensation circuit 205, as well as the FIG. 17 phase compensation circuit 203, considers each mode of movement and it is configured by proportional plus derivative circuits PD1–PD3 and integral circuits I1–I3 providing their respective outputs which are fed through a distributor 206 for distribution to electromagnets M1–M3 to pass electric current to electromagnets M1–M3 via limit circuits LM1–LM3 and power amplifiers A1–A3.

If the FIG. 16A maglev pumps 1 is used as a mobile pump or it is buried in a human body in the form of a blood pump, the entirety of the pump would move while impeller 23 rotates. Furthermore, the FIG. 16A impeller 23 in the form of a disc pitches and yaws as it rotates, and the entirety of the pump is thus affected by gyroscopic moment, disadvantageously resulting in precession, swaying around.

If impeller 23 is rotating and pitching and yawing movements are applied to the pump, a gyroscopic moment proportional to the movements' speed acts on impeller 23. This gyroscopic moment results in impeller 23 being affected by a gyroscopic moment having an axis of rotation orthogonal to a rotative movement, such as pitching, applied to the pump as disturbance and impeller 23 thus displaces in pump chamber 22, and triggered thereby is a precession of a low frequency in the direction opposite to the direction in which impeller 23 rotates.

In particular, if the pump is used as a blood pump and the precession results in casing 21 and impeller 23 contacting with each other, thrombus readily forms there. Thus, desirably the precession should be minimized. The precession may be reduced by increasing the size of the electromagnet to enhance the stiffness of the magnetic bearing, although such cannot be adopted if the pump is used as a blood pump implanted in a body as it is required to be minimized.

SUMMARY OF THE INVENTION

Therefore the present invention mainly contemplates a maglev pump and a circuit controlling the same without requiring the pump to be increased in size, capable of steadily supporting a rotating impeller by compensating for a gyroscopic moment introduced in response to a disturbance applied to the pump when the pump is used in the form of a mobile pump.

The present invention provides a maglev pump including: an impeller in the from of a disc magnetically levitated and thus rotated for delivery of fluid, the impeller having one surface provided with a first ferromagnetic body and the other surface circumferentially provided with a second ferromagnetic body; an electromagnet closer to one side of the impeller to face the first ferromagnetic body to attract the impeller toward one side; a permanent magnet arranged closer to the other side of the impeller circumferentially to face the second ferromagnetic body; and a mechanism arranged closer to one side of the impeller to transmit to the impeller without contacting the impeller a force driving and thus rotating the impeller, wherein the impeller is magnetically levitated by controlling an electric current flowing through the electromagnet to provide in balance an attractive force provided by the electromagnet and applied to the second ferromagnetic body, an attractive force provided by the electromagnet and applied to the first ferromagnetic body, and a force generated by the mechanism to act on the impeller in the direction of an axis of rotation.

Since an electromagnet of a magnetic bearing can be arranged closer to the mechanism transmitting a force driving and thus rotating the impeller, the pump can be reduced in length in the axial direction and thus miniaturized. Furthermore, a permanent magnet serving to additionally provide a passive magnetic bearing can enhance the stiffness of the impeller in the radical direction.

Preferably, the impeller has one side circumferentially provided with a first electromagnet, and the mechanism includes a rotor having the other surface circumferentially provided with a second permanent magnet opposite the first permanent magnet, and having one surface serving as a motor rotor, and a motor stator provided opposite one side of the motor rotor.

Arranging the electromagnet closer to the motor can reduce the length of the magnetic bearing unit in the axial direction.

More preferably, the ferromagnetic body is arranged closer to an inner diameter of the impeller opposite the electromagnet and the first permanent magnet is arranged closer to an outer diameter of the impeller circumferentially, and the electromagnet is arranged closer to an inner diameter and the motor rotor is arranged closer to an outer diameter.

More preferably, the first permanent magnet is arranged closer to an inner diameter of the impeller circumferentially and the first ferromagnetic body is arranged closer to an outer diameter of the impeller opposite the electromagnet, and the motor rotor is arranged closer to an inner diameter and the electromagnet is arranged closer to an outer diameter.

Arranging the electromagnet closer to the outer diameter allows the electromagnet to have an increased winding space.

More preferably the mechanism includes a motor rotor arranged closer to one side of the impeller and a motor stator arranged opposite the motor rotor.

Thus a motor and a motor bearing supporting the rotor can be dispensed with.

The present invention in another aspect provides a control circuit controlling a magnetically levitated pump, applying an electromagnetic attractive force in one direction of an impeller and at least one of a magnetic attractive force to support the impeller without contacting the impeller, the control circuit having a sensor detecting a position of the impeller and an electromagnet applying the electromagnetic attractive force to the impeller to position the impeller, including: a separation circuit driven by an output of the sensor to separate a movement of the impeller into a translative movement in a direction of an axis of rotation of the impeller, a pitching movement and a yawing movement; a phase compensation circuit including a proportional-plus-derivative circuit and one of an integral circuit and a lowpass circuit in parallel with the proportional-plus-derivative circuit for each movement provided by the separation circuit; and a limit circuit connected to the phase compensation circuit at one of an input and an output of one of the integral circuit and the lowpass circuit controlling the translative movement.

Preferably, when the integral circuit controlling the translative movement outputs a signal indicating that the impeller leans closer to the electromagnet than a position set for the impeller to be levitated, the limit circuit disconnects one of the input and the output of one of the integral circuit and the lowpass circuit.

Preferably, the limit circuit limits the output of the integral circuit controlling the translative movement, to a signal of one of positive and negative outputs of one of the input and the output of one of the integral circuit and the lowpass circuit.

The present invention in still another aspect provides a control circuit controlling a magnetically levitated pump, applying an electromagnetic attractive force in one direction of an impeller and at least one of a magnetic attractive force to support the impeller without contacting the impeller, the control circuit having a sensor detecting a position of the impeller and an electromagnet applying the electromagnetic attractive force to the impeller to position the impeller, including: an operation circuit operative in response to an output of the sensor to perform an operation to calculate a distance between the electromagnet and the impeller; a phase compensation circuit including in parallel a proportional plus derivative circuit and one of an integral circuit and a lowpass circuit receiving a signal output from the operation circuit; and a limit circuit connected to one of an input and an output of one of the integral circuit and the lowpass circuit.

Preferably, when the integral circuit controlling the translative movement outputs a signal indicating that the impeller leans closer to the electromagnet than a position set for the impeller to be levitated, the limit circuit disconnects one of the input and the output of one of the integral circuit and the lowpass circuit.

Preferably, the limit circuit limits the output of the integral circuit controlling the translative movement, to a signal of one of positive and negative outputs of one of the input and the output of one of the integral circuit and the lowpass circuit.

More preferably the maglev pump is used for blood circulation.

The present invention in still another aspect provides a control circuit controlling a magnetically levitated pump, applying an electromagnetic attractive force in one direction of an impeller and at least one of a magnetic attractive force to support the impeller without contacting the impeller, the control circuit having a sensor detecting a position of the impeller and an electromagnet applying the electromagnetic attractive force to the impeller to position the impeller, including: a separation circuit driven by an output of the sensor to separate a movement of the impeller into a translative movement in a direction of an axis of rotation of the impeller, a pitching movement and a yawing movement; a phase compensation circuit applying proportional, derivative and integral elements for each of the translative, pitching and yawing movements to control an electromagnetic attractive force of the electromagnet; and a filter circuit extracting only a low frequency component from each movement parameter for addition to an input of the phase compensation circuit controlling the pitching and yawing movements, wherein compensation is made for a gyroscopic moment introduced when the impeller is rotating.

The present invention in still another aspect provides a control circuit controlling a magnetically levitated pump, applying an electromagnetic attractive force in one direction of an impeller and at least one of a magnetic attractive force to support the impeller without contacting the impeller, the control circuit having a plurality of sensors detecting a position of the impeller and a plurality of electromagnets applying the electromagnetic attractive force to the impeller to position the impeller, including: an operation circuit operative in response to an output of the sensor to perform an operation to calculate a distance between the electromagnet and the impeller; a phase compensation circuit controlling an electromagnetic attractive force of each of the electromagnets via proportional, derivative and integral elements receiving a signal output from the operation circuit; and a filter circuit extracting a low frequency component from a signal obtained from an operation calculating a distance between an adjacent one of the electromagnets and the impeller, wherein an output of the filter circuit is added to compensate for a gyroscopic moment introduced when the impeller is rotating.

Furthermore, the present invention in another aspect provides a control circuit controlling a magnetically levitated pump, applying an electromagnetic attractive force in one direction of an impeller and at least one of a magnetic attractive force to support the impeller without contacting the impeller, the control circuit having a plurality of sensors detecting a position of the impeller and a plurality of electromagnets applying the electromagnetic attractive force to the impeller to position the impeller, including: an operation circuit operative in response to an output of the sensor to perform an operation to calculate a distance between the electromagnet and the impeller; a phase compensation circuit controlling an electromagnetic attractive force of each of the electromagnets via proportional, derivative and integral elements receiving a signal output from the operation circuit; and an addition circuit adding only a signal output from a corresponding the integral element and an output of an adjacent the phase compensation circuit together, wherein compensation is made for a gyroscopic moment introduced when the impeller is rotating.

Thus in the present invention if the pump is used in the form of a mobile pump, compensation can be made for a gyroscopic moment introduced in response to a rotative disturbance applied to the pump, and the impeller can thus be supported steadily as it rotates.

Still more preferably the pump includes a circuit detecting a rotation speed of the impeller to alter a level of compensation for the gyroscopic moment.

Still more preferably the maglev pump is used for blood circulation.

The foregoing and other objects, features, aspects and advantages of the present invention will become more apparent from the following detailed description of the present invention when taken in conjunction with the accompanying drawings.

BRIEF DESCRIPTION OF THE DRAWINGS

In the drawings:

FIGS. 14A–14E represent signals of different components and the impeller's movement when with the FIG. 9 integral circuit replaced with a lowpass circuit a stepwise disturbance is applied on that side of the impeller facing the electromagnet;

DESCRIPTION OF THE PREFERRED EMBODIMENTS

Figure 1:
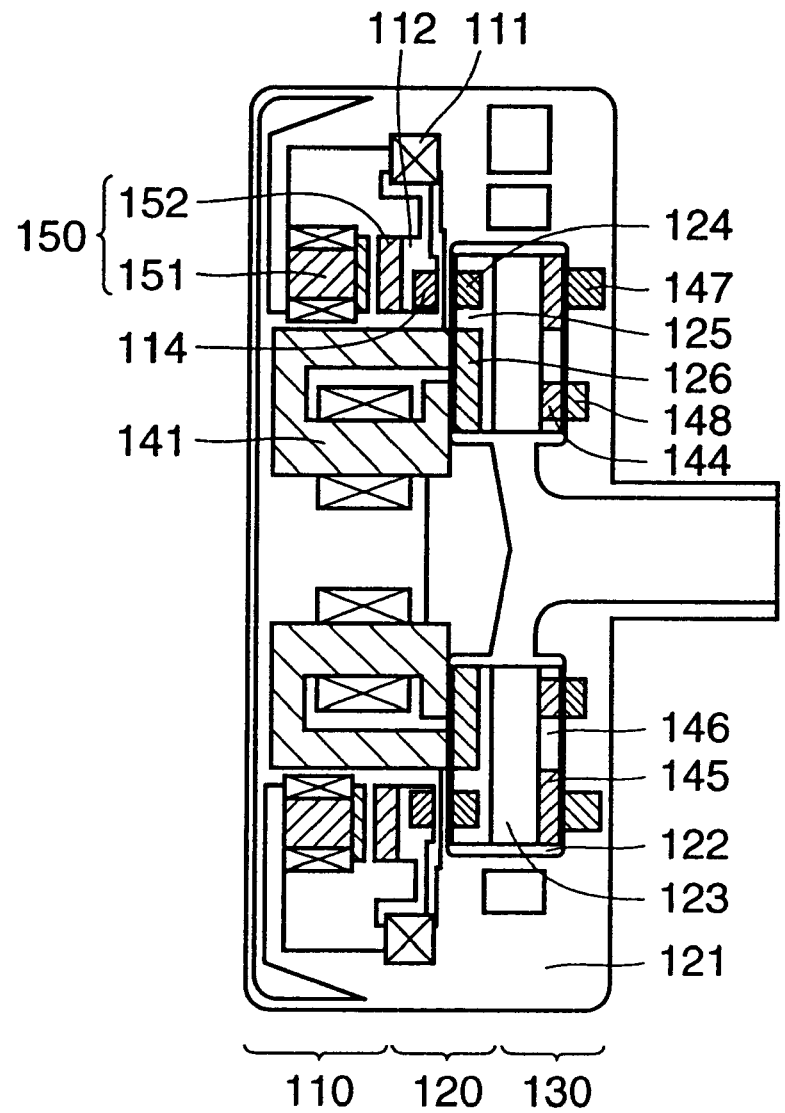
FIG. 1 is a vertical cross section of a maglev pump of one embodiment of the present invention.

FIG. 1 is a vertical cross section of a maglev pump of one embodiment of the present invention. As shown in FIG. 1, the maglev pump is configured by an actuator unit 110, a pump unit 120 and an anti-motor unit 130. In pump unit 120 internal to a casing 121 is provided a pump chamber 122 and therein an impeller 123 rotates.

Casing 121 is formed for example of plastic, ceramic, metal or the like, although of casing 121 a partition between actuator unit 110 and impeller 123 and that between anti-motor unit 130 and impeller 123 are formed of non-magnetic material as they are not allowed to be formed of magnetic material. Impeller 123 has one end (a left-hand end in FIG. 1) provided with a non-magnetic member 125 having a permanent magnet 124 for a non-controlled magnetic bearing, and a soft magnetic member 126 corresponding to a rotor of a controlled magnetic bearing. Permanent magnet 124 is divided in a direction of a circumference of impeller 123 and adjacent permanent magnets 124 are magnetized to have opposite magnetic poles. Impeller 123 has the other end (a right-hand end in FIG. 1) provided with a non-magnetic member 146 including a ferromagnetic body 144, including a permanent magnet or a soft magnetic material, in the form of a ring constituting a non-controlled magnetic bearing, and a soft magnetic member 145 serving as a sensor target.

Opposite to that side of impeller 123 having permanent magnet 124 is provided a rotor 112, external to pump chamber 122, supported by a motor bearing 111 provided for example by a rolling bearing, a hydrodynamic bearing, or the like. Rotor 112 is driven and thus rotated by an 6 axial gap motor formed by a motor stator 151 and a motor rotor 152 arranged axially opposite each other. Rotor 112 is provided with the same number of permanent magnets 114 as permanent magnets 124 of impeller 123, opposite permanent magnets 124 to exert attractive force. Adjacent permanent magnets 114 are also magnetized to have opposite magnetic poles.

Thus, as shown in FIG. 1, motor unit 150 is a synchronous motor provided by a DC motor, although it may be any type of motor, such as an asynchronous motor including an induction motor.

An electromagnet 141 is provided opposite soft magnetic member 126 of impeller 123. Furthermore, a position sensor 147 is arranged opposite soft magnetic member 145 of impeller 123, and a permanent magnet in the form of a ring 148 is arranged opposite ferromagnetic body 144.

In FIG. 1, permanent magnet 148 opposite ferromagnetic body 144 is arranged closer to an internal diameter of impeller 123 to reduce disturbance for pitching and yawing to impeller 123 attributed to attractive force acting between the members.

Furthermore, impeller 123 can move in pump chamber 122 axially and within this allowed range of movement an attractive force between permanent magnet 148 and ferromagnetic body 144 is maintained constantly greater than that between permanent magnets 124 and 114 by forming each of permanent magnet 148 and ferromagnetic body 144 of an appropriate material and shaping them, as appropriate, and positioning permanent magnet 148, as appropriate.

Position sensor 147 and electromagnet 141 allow impeller 123 to be held at a center of pump chamber 122 in balance with the attractive force of permanent magnets 124 and 114 and that of ferromagnetic body 144 and permanent magnet 148 in pump chamber 122. Herein, a ferromagnetic body (including a permanent magnet and a soft magnetic material) is arranged closer to a rotor of a non-controlled magnetic bearing unit additionally provided, although if the ferromagnetic body is a permanent magnet, opposite permanent magnet 148 may be replaced by soft magnetic material.

Figure 16A:
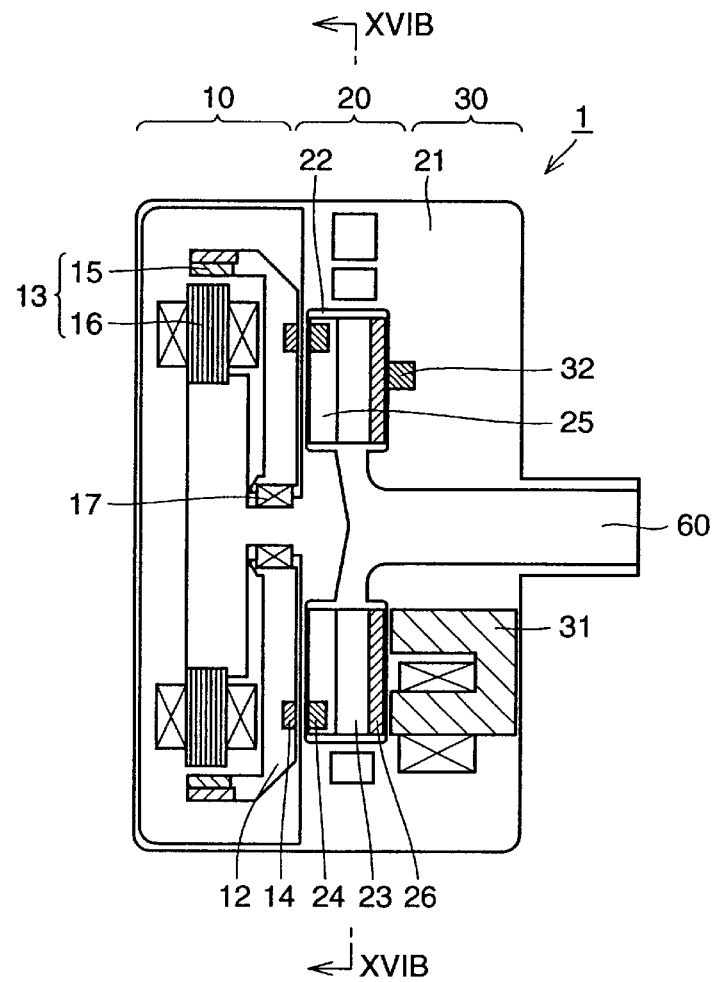
FIGS. 16A and 16B are cross sections of a conventional maglev pump.
Figure 16B:
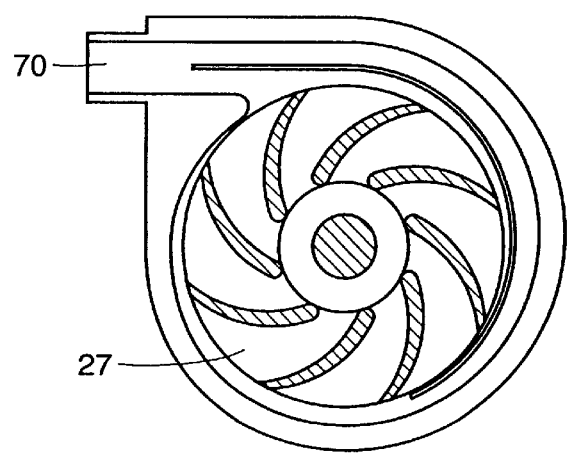

As has been described above, in the FIG. 1 embodiment electromagnet 141 is arranged closer to motor unit 110 the conventional, FIG. 16A magnetic bearing unit 30 or FIG. 1 anti-motor unit 130 can be reduced in axial length and furthermore, allowing ferromagnetic body 144 of impeller 123 and permanent magnet 148 opposite thereto to additionally provide a non-controlled magnetic bearing, can enhance the radial stiffness of impeller 123.

Furthermore, while in FIG. 1 position sensor 147 is arranged in anti-motor unit 130, it may be arranged in a vicinity of an electromagnet, as has been described in the conventional example shown in FIG. 16A.

Figure 2:
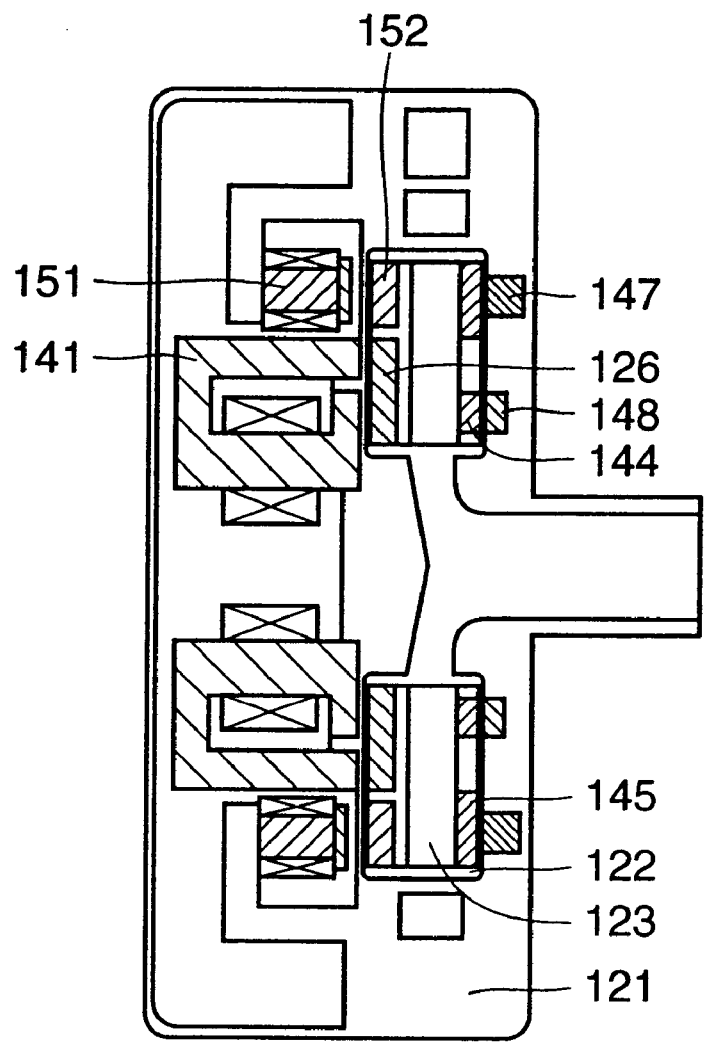
FIG. 2 is a vertical cross section of the maglev pump of another embodiment of the present invention.

FIG. 2 is a vertical cross section of the maglev pump of another embodiment of the present invention. The FIG. 2 pump is similar in configuration to the FIG. 1 pump, except that the former has impeller 123 rotatively driven in a different system. In FIG. 1 rotor 112 is rotated and its internal permanent magnet 114 and permanent magnet 124 of impeller 123 provide magnetic-coupling to rotate impeller 123, whereas in the FIG. 2 embodiment impeller 123 is internally provided with motor rotor 152 and from motor stator 151 external to the pump chamber a rotating magnetic field is directly applied to rotate impeller 123.

In this example, an attractive force acting between motor rotor 152 and motor stator 151, an electromagnetic attractive force of electromagnet 141 and an attractive force acting between ferromagnetic body 144 and permanent magnet 148 serving as a non-controlled magnetic bearing, can be balanced by controlling electromagnetic attractive force to provide non-contact, magnetic levitation of impeller 123. More specifically, permanent magnet 148 and ferromagnetic body 144 is each formed of an appropriate material and shaped as appropriate and permanent magnet 148 is positioned as appropriate so that between ferromagnetic body 144 and permanent magnet 148 serving as the non-controlled magnetic bearing there acts an attractive force greater than that acting between motor stator and rotor 151 and 152 within the impeller's operation range in pump chamber 122 and between motor stator and rotor 151 and 152 there acts an attractive force varying with the motor load that has a maximum value constantly smaller than an attractive force acting between permanent magnet 148 and ferromagnetic body 144.

Thus rotor 121 and a motor bearing supporting the same can be dispensed with and the structure can be simplified advantageously. Furthermore, while herein a ferromagnetic body (including a permanent magnet and a soft magnetic material) is arranged closer to a rotor of a non-controlled magnetic bearing unit additionally provided, opposite permanent magnet 148 may be replaced by soft magnetic material if the ferromagnetic body is a permanent magnet.

Figure 3:
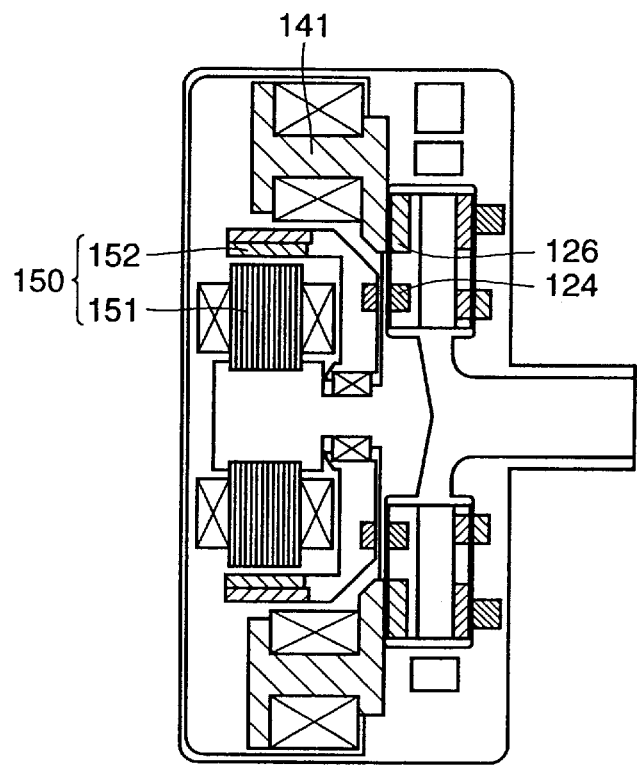
FIG. 3 is a cross section of the maglev pump of still another embodiment of the present invention.

FIG. 3 is a vertical cross section of the maglev pump of the present invention in still another embodiment. The FIG. 3 pump is substantially similar in configuration to the FIG. 1 pump, except that in the former, motor 150 is arranged closer to an inner diameter and electromagnet 141 is arranged closer to an outer diameter. Accordingly, impeller 123 has soft magnetic material 126 arranged closer to the outer diameter and permanent magnet 124 arranged closer to the inner diameter. As shown in FIG. 3, electromagnet 141 arranged closer to the outer diameter allows electromagnet 141 to have an increased winding space. This can reduce consumption (copper losses) at an electromagnet coil portion and also increase the radius of a force (attractive force) introduced by electromagnet 141 to act on impeller 123, and impeller 123 has pitching and yawing characteristics more advantageous than in the embodiments shown in FIGS. 1 and 2.

Figure 4:
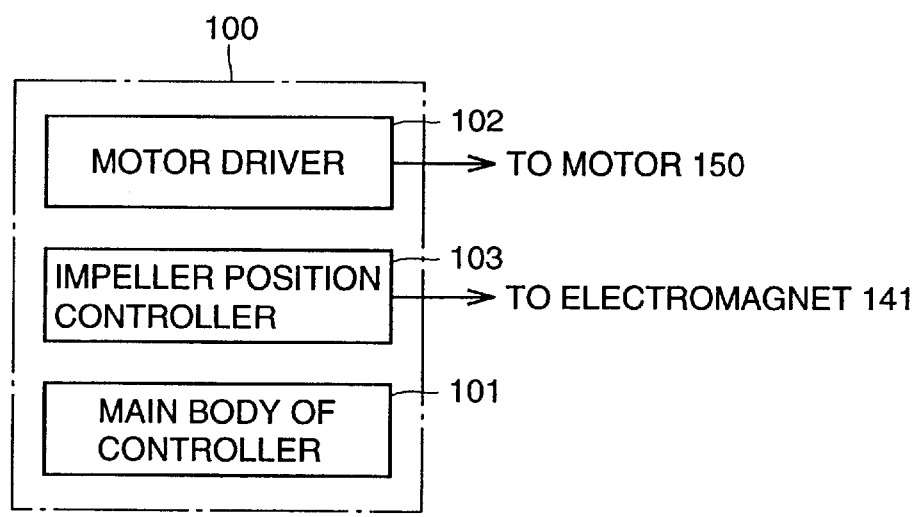
FIG. 4 is a schematic block diagram showing a control circuit driving a maglev pump of the present invention.

FIG. 4 is a block diagram showing a control circuit operative to drive a maglev pump of one embodiment of the present invention. As shown in FIG. 4, a controller 100 includes an impeller levitation position control function employing an impeller position control function, an impeller rotation torque control function and an impeller position control function to alter a position of impeller 123 in pump chamber 122 as the impeller levitates.

More specifically, controller 100 includes a main body 101 of the controller, a motor driver 102 and an impeller position controller 103. Motor driver 102 outputs a voltage corresponding to a motor rotation speed output from main body 101, to rotate motor 150. Impeller position controller 103 is operative to maintain a position of the impeller for levitation that is output from main body 101. More specifically, impeller position controller 103 controls current or voltage or current and voltage flowing through electromagnet 141. Position sensor 147 outputs a detection which is input to impeller position controller 103 controlling an electric current through electromagnet 141 to control a translative movement of impeller 123 in the direction of its center axis (an axis z) and rotative movements thereof around axes x and y orthogonal to the center axis z.

Thus in the present embodiment an electromagnet of a magnetic bearing can be arranged closer to a rotation transmitting mechanism to reduce the pump in length in the axial direction to miniaturize the same. As a result, if the maglev pump of the present invention is used as a blood pump to be implanted in a body it can readily be implanted in the body. Furthermore, adding a non-controlled magnetic bearing can enhance stiffness in the direction of a radius of the impeller and thus increase a tolerable disturbance value of the pump.

Figure 5:
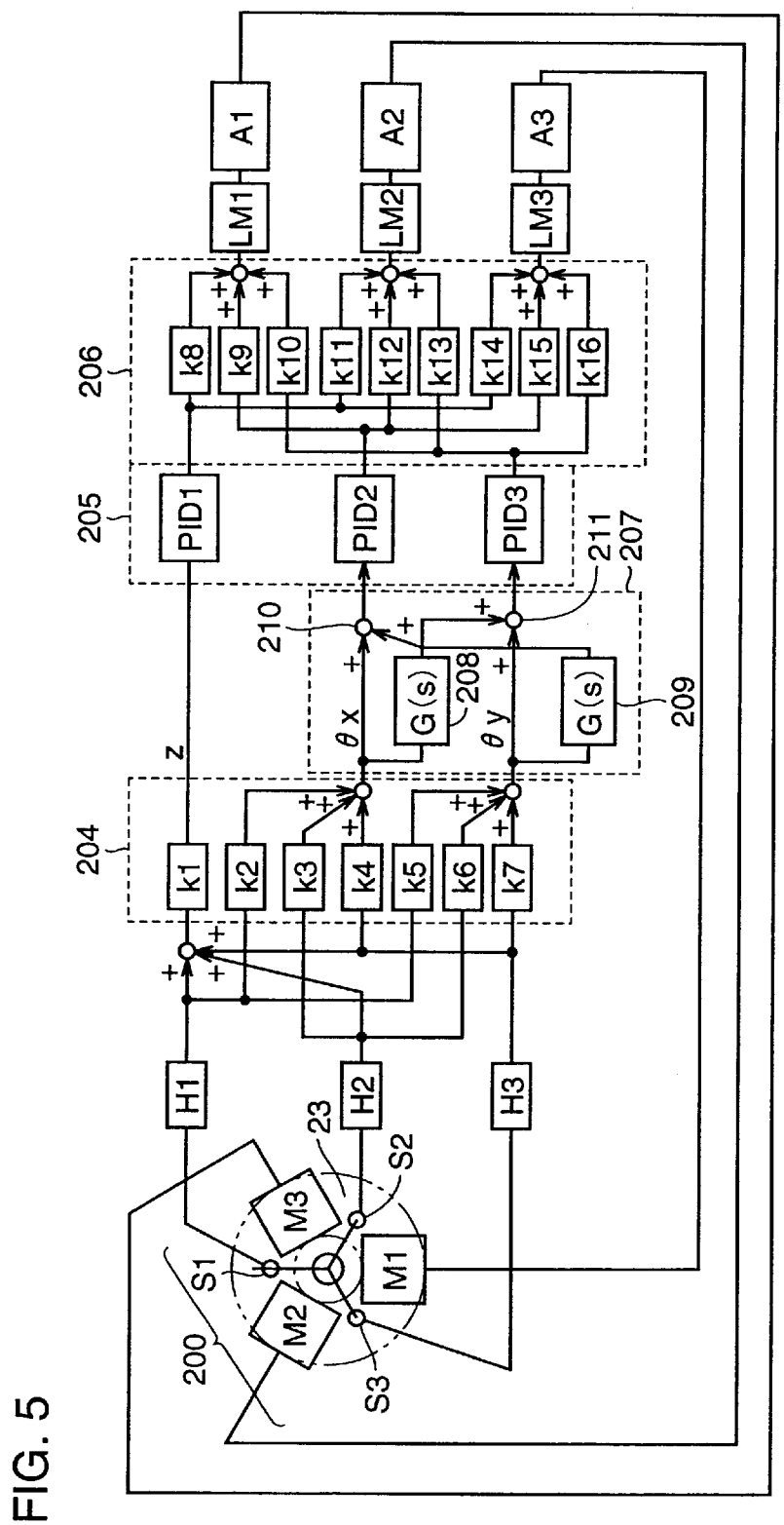
FIGS. 5–9 are a block diagrams each showing the circuit controlling the maglev pump in still another embodiment of the present invention.

FIG. 5 is a block diagram of a maglev pump and a control circuit in another embodiment of the present invention.

As has been described in the conventional art, when impeller 23 is rotating and pitching and yawing movements are applied to the pump, a gyroscopic moment proportional to the movements' speed acts on impeller 23. This gyroscopic moment results in impeller 23 being affected by a gyroscopic moment having an axis of rotation orthogonal to a rotative movement (e.g., pitching) applied to the pump as disturbance and impeller 23 thus displaces in pump chamber 22, and furthermore triggered thereby is a precession at a low frequency in a direction opposite the direction in which impeller 23 rotates. This is attributed to interference of the impeller's pitching and yawing movements attributed to gyroscopic moment. The precession can be reduced simply by compensation via a magnetic bearing control circuit in the frequency of the precession to eliminate the interference of the two rotative movements.

Figure 18:
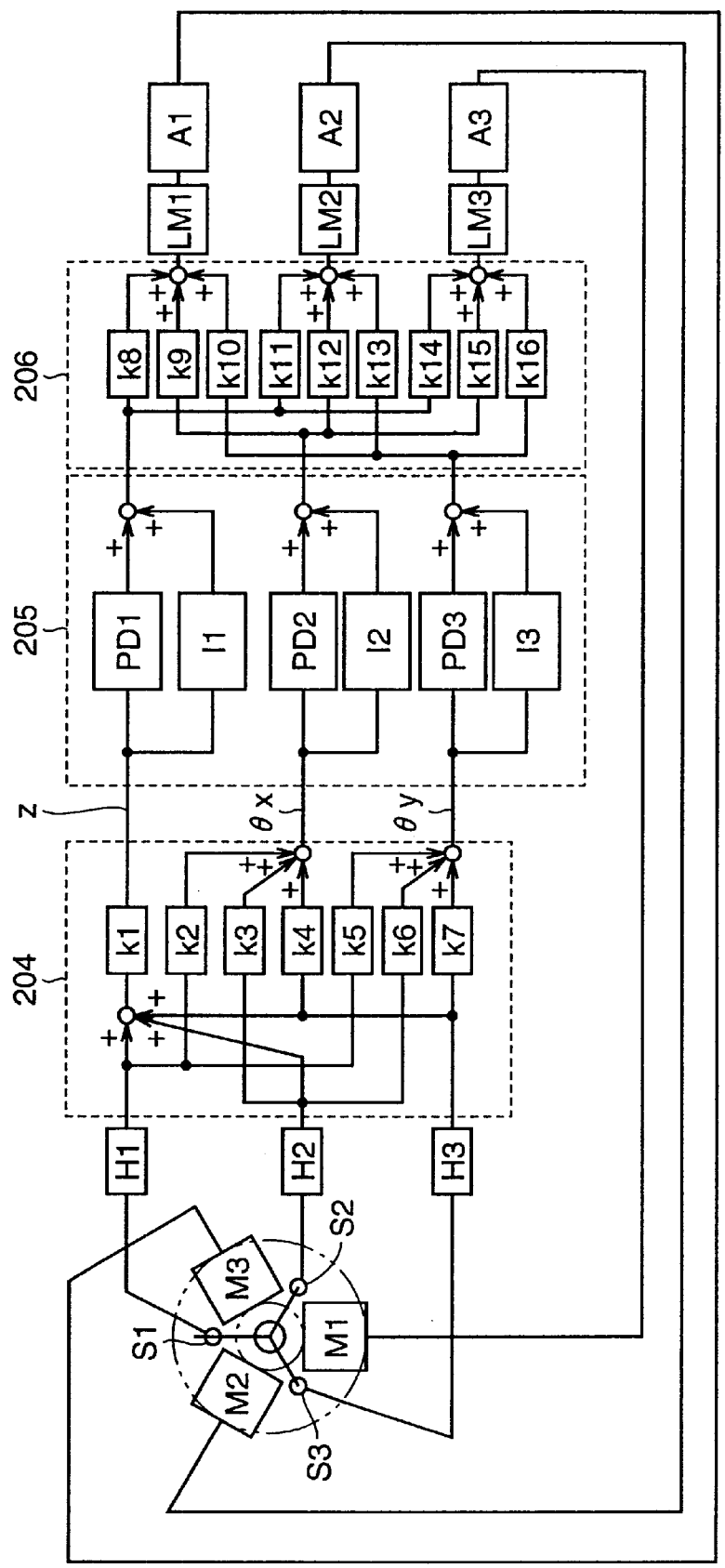
FIG. 18 is a block diagram showing another example of the circuit controlling the maglev pump shown in FIGS. 16A and 16B.

Thus in the present embodiment a configuration is provided to eliminate the interference of the two rotative movements in the frequency range of the precession. More specifically, as well as shown in FIG. 18, a maglev pump is shown in a perspective view, as seen at suction port 60 shown in FIG. 16A, and three electromagnets M1–M3 and three sensors S1–S3 are arranged to surround an axis of rotation of impeller 23. Sensors S1–S3 provide their respective outputs which are input to sensor amplifiers H1–H3 and amplified thereby for input to separation circuit 204, which, as well as shown in FIG. 18, performs an operation on sensor signals received from sensor amplifiers H1–H3 to output the impeller 23 translative movement parameter z, pitching movement parameter θx and yawing movement parameter θy.

Parameter z is applied to phase compensation circuit 205, whereas parameters θx and θy are applied to a circuit 207 configured by circuits 208 and 209 configured by a lowpass filter and a gain circuit and addition circuits 210 and 211. The lowpass filter of circuits 208, 209 extracts a precession component having a main component in a low frequency of impeller movement and addition circuits 210, 211 add the extracted precession component to a control input of a different mode of rotative movement to reduce interference of the two rotative movements. The gyroscopic moment has an effect varying with the impeller 23 rotation speed, and different rotation speed of impeller 23 can change the circuit 207 characteristics to achieve optimized compensation.

Addition circuits 210, 211 provide an output which is in turn applied to phase compensation circuit 205 and via distributor 206, limit circuits LM1–LM3 and power amplifiers A1–A3 an electric current is passed through each of electromagnets M1–M3.

As has been described above, in the present embodiment an impeller's pitching movement parameter θx and yawing movement parameter θy can be applied to circuit 207, lowpass filter of circuits 208 and 209 extracts a precession component having a main component in a low frequency of the impeller, and addition circuits 210, 211 allow the extracted precession component to be added to a control input of the other mode of rotative movement to reduce interference of the impeller's pitching and yawing movements to provide optimal compensation.

Figure 6:
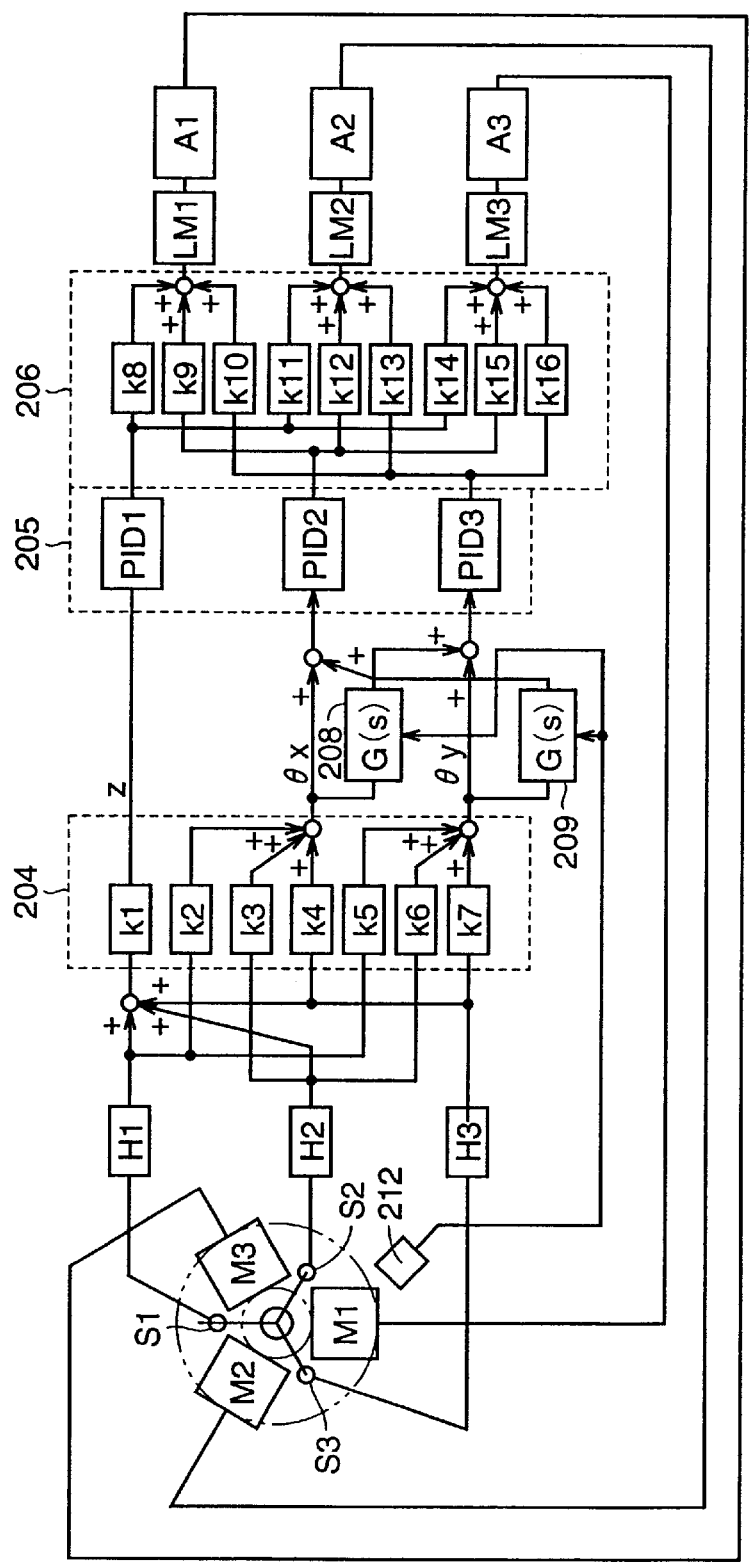

FIG. 6 is a block diagram showing a control circuit of another embodiment of the present invention. In the embodiment shown in FIG. 5 the impeller's rotation speed is not used to alter compensation of precession and in particular when the impeller is not rotating, compensation of circuit 207 acts as disturbance on controlling a magnetic bearing and in effect, circuits 208 and 209 need to have their characteristics previously adjusted so as to allow the magnetic bearing to support impeller 23 steadily when the impeller is not rotating.

In contrast, in the FIG. 6 embodiment an impeller rotation speed detector 212 is provided to detect the impeller 23 rotation speed and detector 212 provides an output in response to which the circuit 208, 209 characteristics vary. Thus in the present embodiment the impeller 23 rotation speed can be used to alter compensation of precession.

Figure 7:
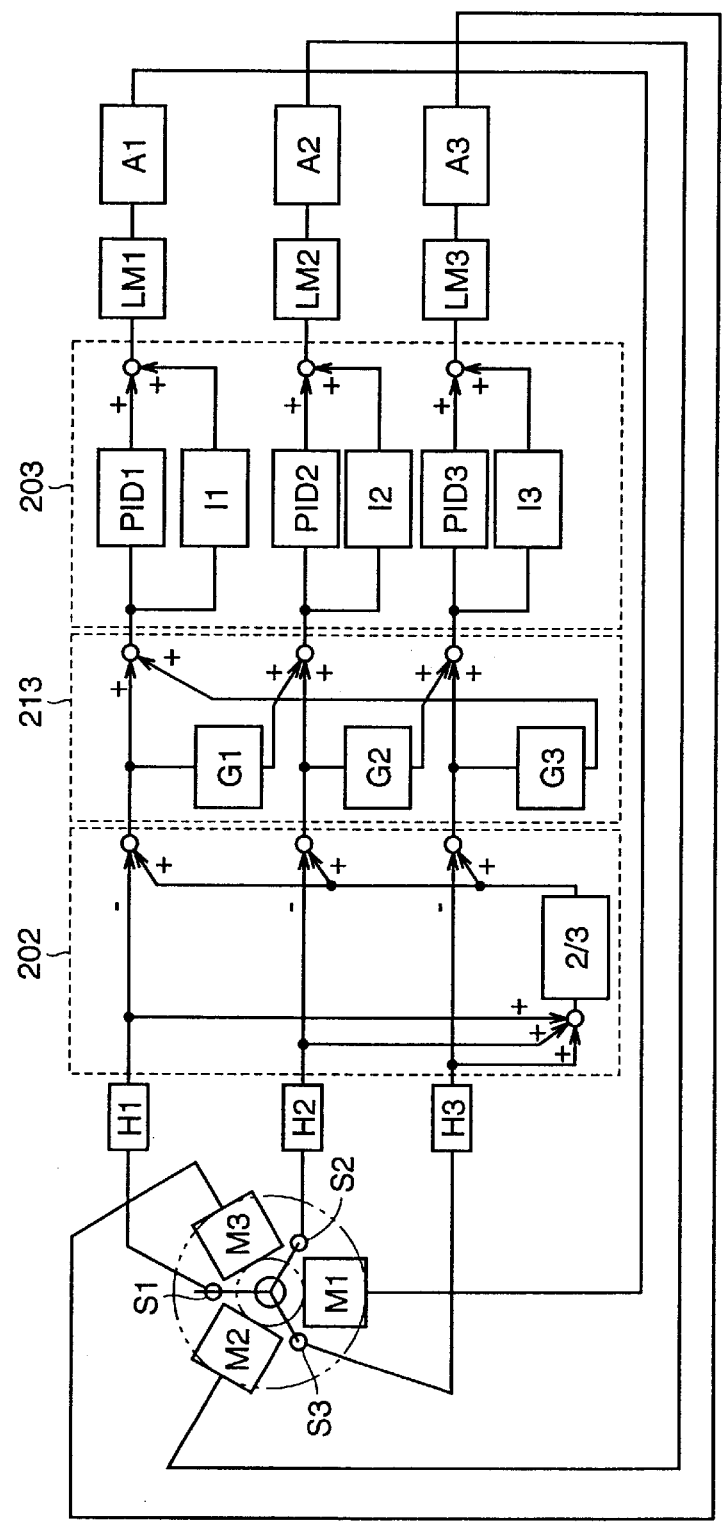

FIG. 7 is a block diagram showing a circuit controlling a maglev pump in still another embodiment of the present invention. The FIG. 7 embodiment corresponds to FIG. 17 conventional control circuit plus circuit 213. In circuit 213, a signal proportional to a distance between each of electromagnets M1–M3 and impeller 23 as a result of an operation on an output of each of sense amplifiers H1–H3, has only a low frequency range thereof added by circuits G1–G3 configured by a proportion circuit and a lowpass filter, to a result of an operation of a distance between an adjacent electromagnet and the impeller to reduce precession attributed to gyroscopic moment.

Figure 8:
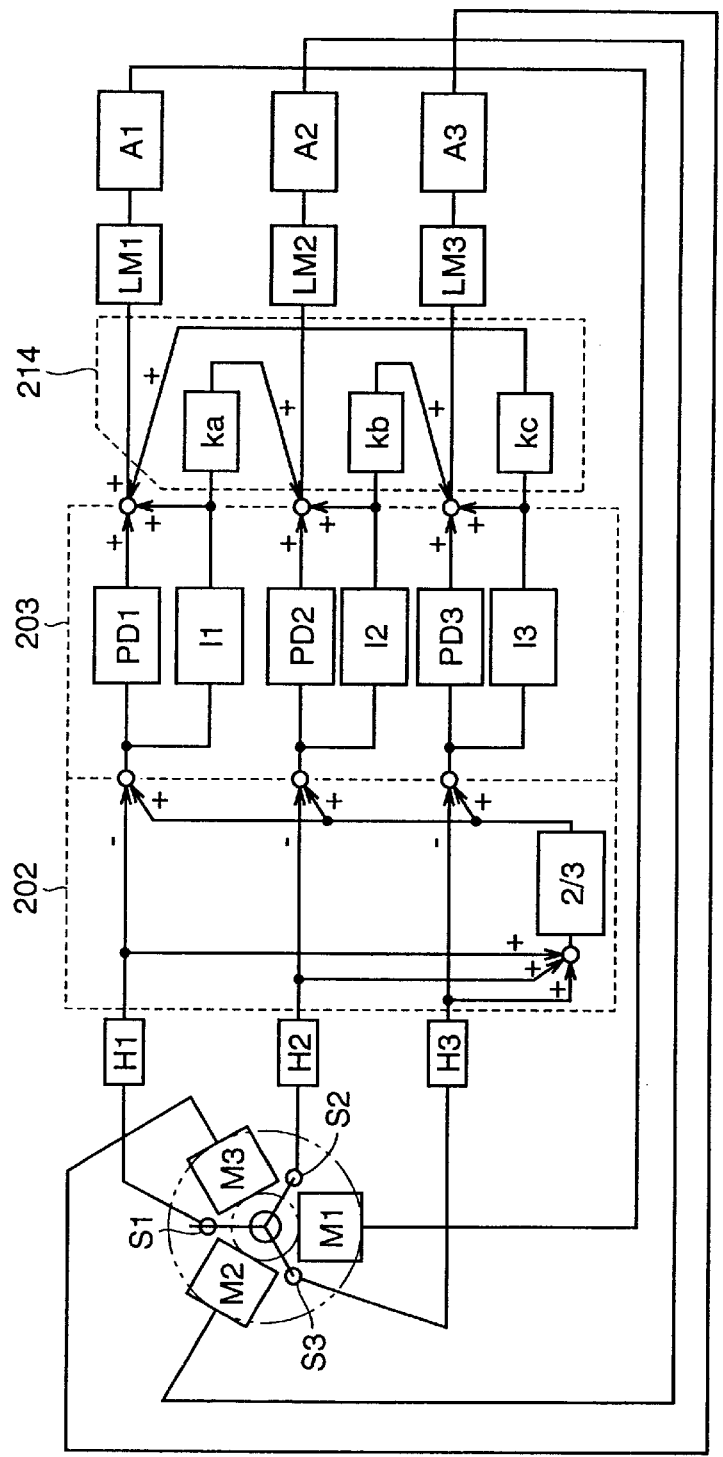

FIG. 8 is a block diagram showing the circuit controlling the maglev pump in still another embodiment of the present invention. The FIG. 8 embodiment corresponds to the FIG. 17 conventional control circuit plus a circuit 214 multiplying outputs of proportional integral circuits I1, I2, I3 of each electromagnetic control by proportional gains ka, kb, kc for addition to adjacent control circuits, respectively.

Note that in the FIG. 6 embodiment using the impeller's rotation speed to alter compensation of precession, is also applicable to the FIGS. 7 and 8 embodiments.

Thus in the present embodiment the pump can have a small size and if the pump is used in the form of a mobile pump it can compensate for gyroscopic moment introduced in response to rotative disturbance applied to the pump and thus support the impeller steadily while the impeller is rotating.

Figure 9:
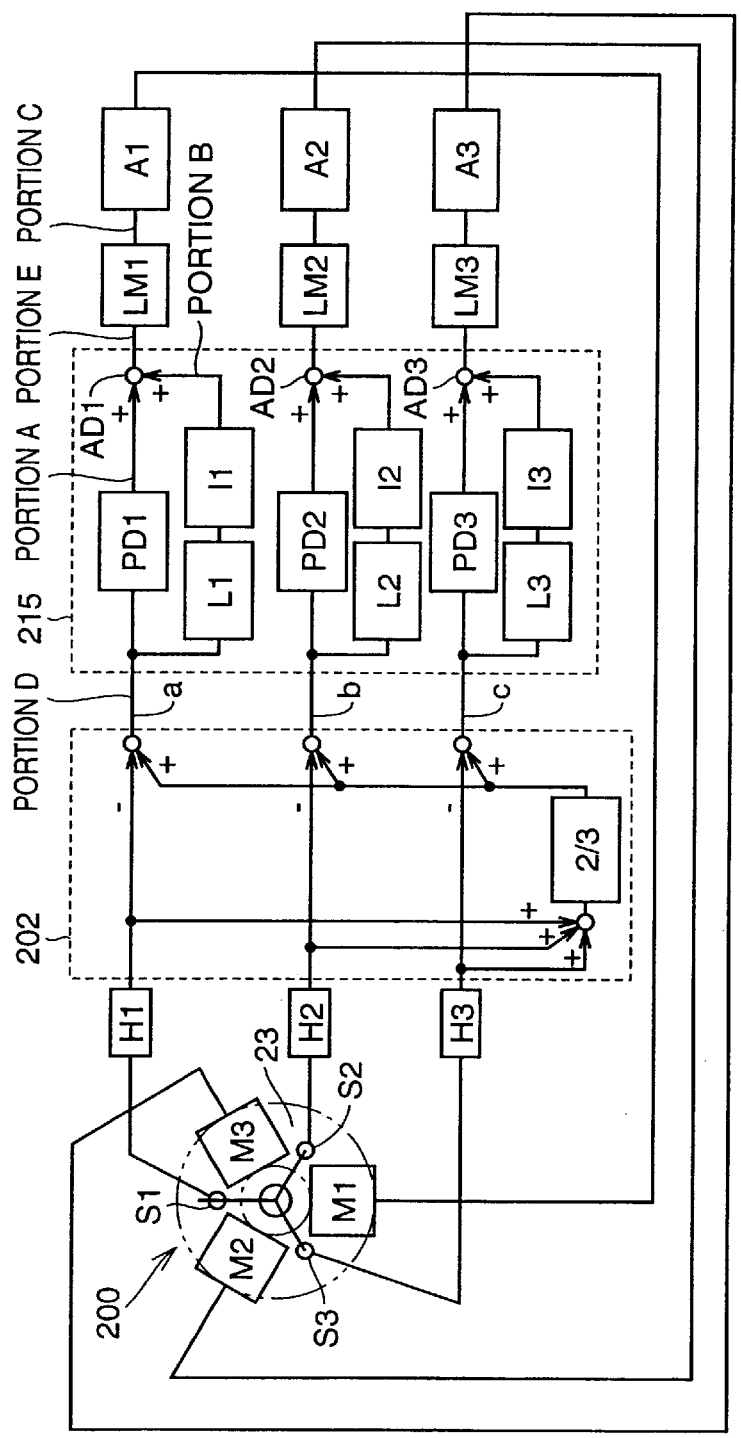

FIG. 9 is a block diagram showing the circuit controlling the maglev pump of still another embodiment of the present invention. The FIG. 9 control circuit corresponds to the FIG. 7 control circuit plus integral circuits I1–I3 preceded by limit circuit L1–L3. More specifically, a maglev pump 200 is shown in a perspective view, as seen at suction port 60 of FIG. 16A, and three electromagnets M1–M3 and three sensors S1–S3 are arranged to surround an axis of rotation of impeller 23. Sensors S1–S3 provide their respective outputs which are input to sense amplifiers H1–H3 and amplified thereby for input to operation circuit 202.

Operation circuit 202 performs an operation on the sensor outputs amplified by sense amplifiers H1–H3 and outputs to a phase compensation circuit 215 a control voltage a proportional to a gap between electromagnet M1 and impeller 23, a control voltage b proportional to a gap between electromagnet M2 and impeller 23, and a control voltage e proportional to a gap between electromagnet M3 and impeller 23.

Phase compensation circuit 215 includes proportional-plus-derivative circuits PD1–PD3 receiving control voltages a, b, c, respectively, limit circuits L1–L3, integral circuits I1–I3 receiving outputs of limit circuits L1–L3, respectively, and an addition circuit AD1 adding outputs of proportional-plus-derivative circuit PD1 and integral circuit I1 together, an addition circuit AD2 adding outputs of proportional-plus-derivative circuit PD2 and integral circuit I2 together and an addition circuit AD3 adding outputs of proportional-plus-derivative circuit PD3 and integral circuit I3 together. Phase compensation circuit 215 provides outputs which are input via limit circuits LM1–LM3 to power amplifiers A1–A3, respectively. Power amplifiers A1–A3 drive their respective electromagnets M1–M3.

In the FIG. 9 control circuit limit circuits L1–L3 only pass a positive-voltage signal input and compulsorily set a negative-voltage signal to be 0V and thus output it to integral circuits I1–I3.

FIGS. 10A–10E represent for the FIG. 9 control circuit a signal of each component and the impeller's movement when a stepwise disturbance is applied on that surface of the impeller facing an electromagnet, and FIGS. 11A–11E represent a signal and the impeller's movement when the FIG. 9 limit circuits L1–L3 are removed and, as well as in FIGS. 10A–10E, a stepwise disturbance is applied on that surface of the impeller facing an electromagnet.

Figure 11A:
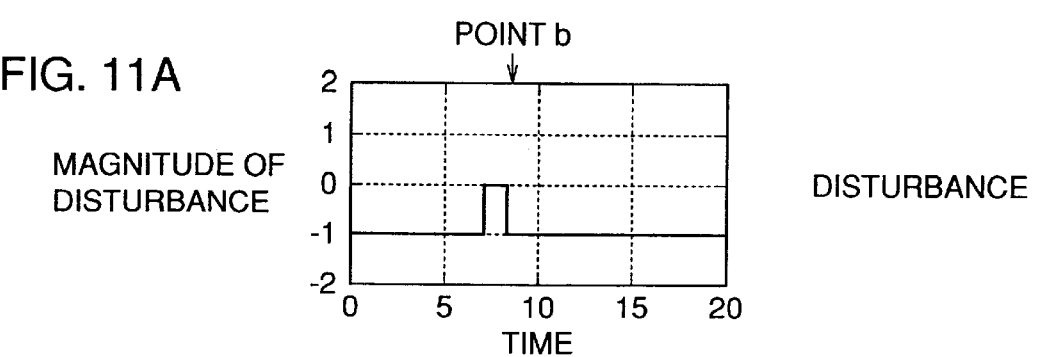
FIGS. 11A–11E represent a signal and the impeller's movement when without the FIG. 9 limit circuit a stepwise disturbance is applied on that side of the impeller facing the electromagnet.
Figure 11B:
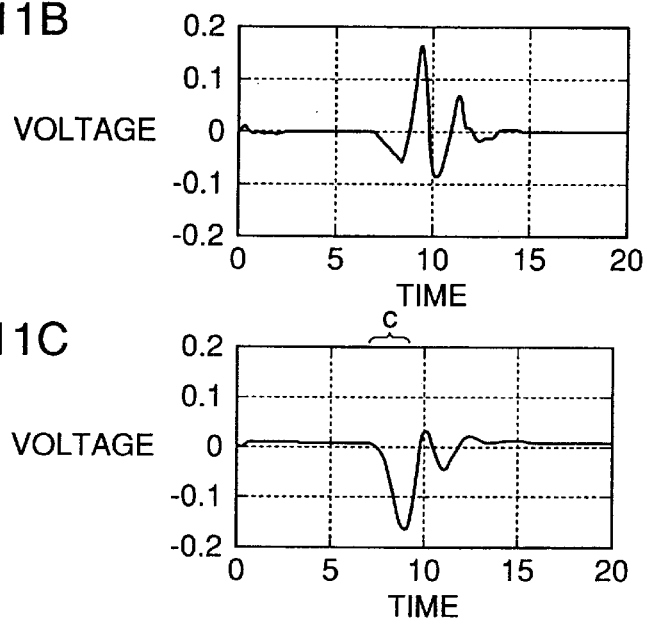
Figure 11C:
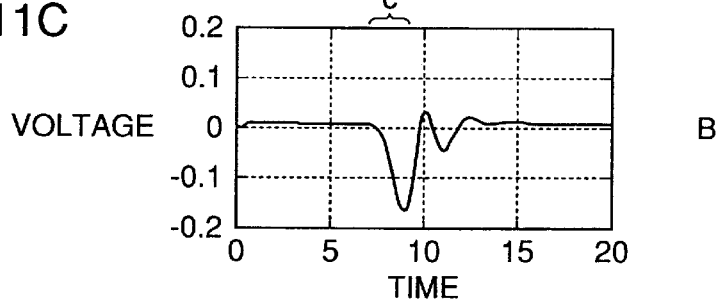

Initially, as is apparent from FIG. 11B, a signal on an output A of the FIG. 9 proportional-plus-derivative circuit PD1 and that on an output B of the FIG. 11C integral circuit I1 present an appearance inverted immediately after the FIG. 11A disturbance is applied. More specifically, it is understood that the integral circuit I1 output is poor in response, which contributes to preventing an output of proportional-plus-derivative circuit PD1 contributing to immediate response and affects a voltage on an output C of FIG. 11D determining a subsequent electromagnet current. As a result, as shown in FIG. 11E, it can be understood from a voltage waveform of a portion D corresponding to the impeller 23 displacement that impeller 23 oscillates significantly.

Figure 10A:
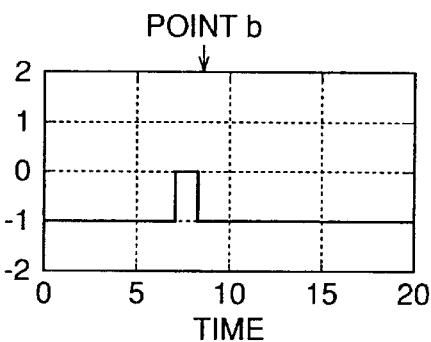
FIGS. 10A–10E represent signals of different components and the impeller's movement when for the FIG. 9 control circuit a stepwise disturbance is applied on that side of the impeller facing the electromagnet.
Figure 10B:
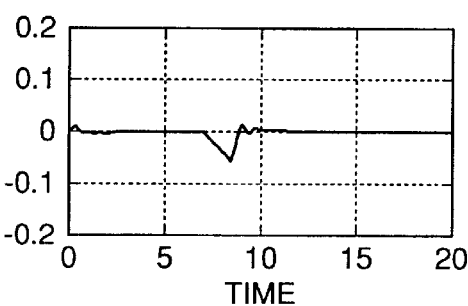
Figure 10C:
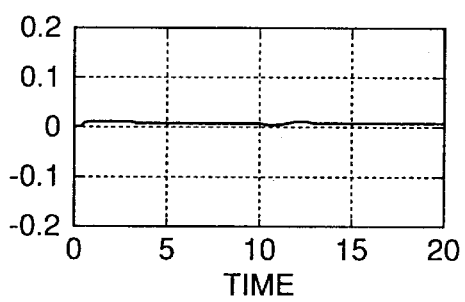
Figure 10D:
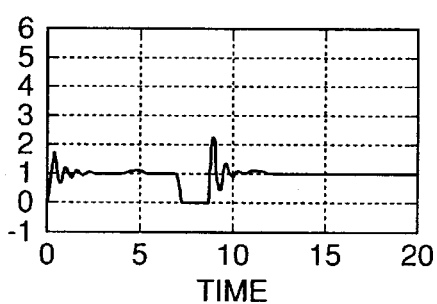
Figure 10E:
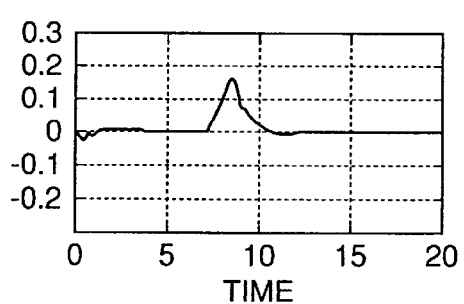

By contrast, if limit circuit L1 precedes integral circuit I1, then, as shown in FIG. 10C, limit circuit L1 prevents integral circuit I1 from receiving a negative signal and voltage on portion B does not have a waveform inhibiting an output of proportional-plus-derivative circuit PD1, as seen in FIG. 10C. As a result, it can be seen from a waveform of a voltage on portion D of FIG. 10E corresponding to the impeller 23 displacement, as compared to that shown in FIG. 11E, that impeller 23 can be free of significant oscillation.

The FIG. 16A maglev pump is configured basically such that an attractive force of electromagnet 31 and that of magnetic-coupling of permanent magnets 14 and 24 are in balance. As such, if impeller 23 receives disturbance having a direction toward electromagnet 31 and also having a magnitude equal to or greater than the attractive force of permanent magnets 14 and 24, electromagnet 31 cannot act to produce a force moving impeller 23 toward the magnetic-coupling.

Figure 11D:
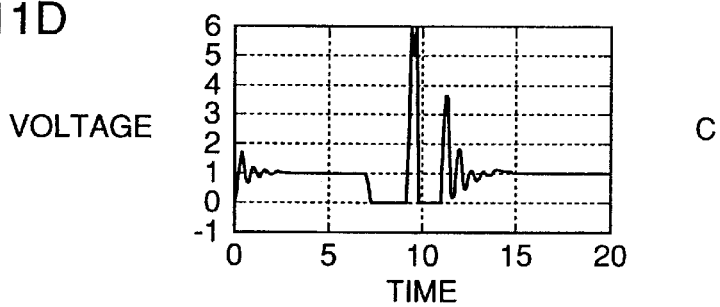
Figure 11E:
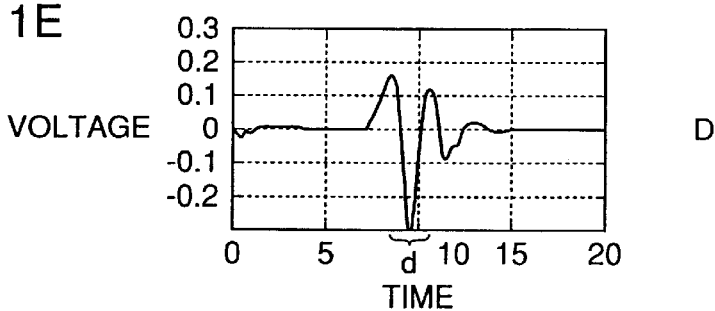
Figure 17:
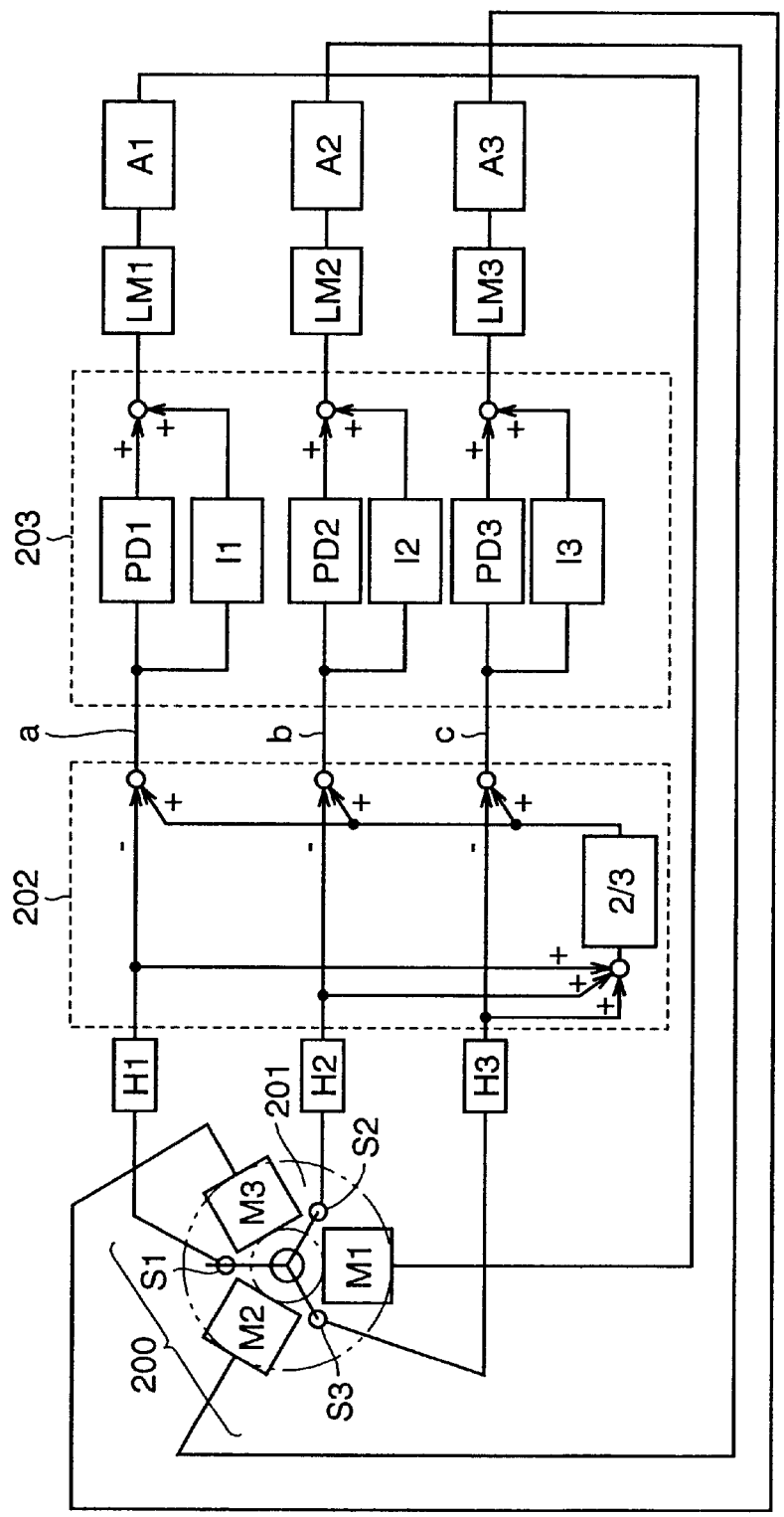
FIG. 17 is a block diagram showing a circuit controlling the maglev pump shown in FIGS. 16A and 16B.

Thus impeller 23 would move toward electromagnet 31, when in the conventional circuit configuration shown in FIGS. 17 and 18 the FIG. 11D integral circuit output would accumulate a negative input value (i.e., a condition with impeller 23 closer to electromagnet 31) and then immediately after the disturbance no longer exists (as shown in FIG. 11A indicated by a point b), with integral circuit I1 having its output increased, if proportional-plus-derivative circuit PD1 outputs a positive voltage the integral circuit I1 output results in adder AD1 providing an addition in a signal having a negative voltage. Consequently, in electromagnet 31, as represented by a point d of a waveform of voltage on portion D of FIG. 11E corresponding to the impeller 23 displacement, immediately after disturbance is eliminated impeller 23 would move toward the magnetic-coupling.

In contrast, in the FIG. 9 embodiment limit circuit L1 can be connected to precede integral circuit I1 to prevent integral circuit I1 from integrating a negative voltage and immediately after disturbance is eliminated the proportional-plus-derivative circuit PD1 output allows electric current to be effectively passed to electromagnet 31 to position impeller 23, as appropriate.

Figure 12:
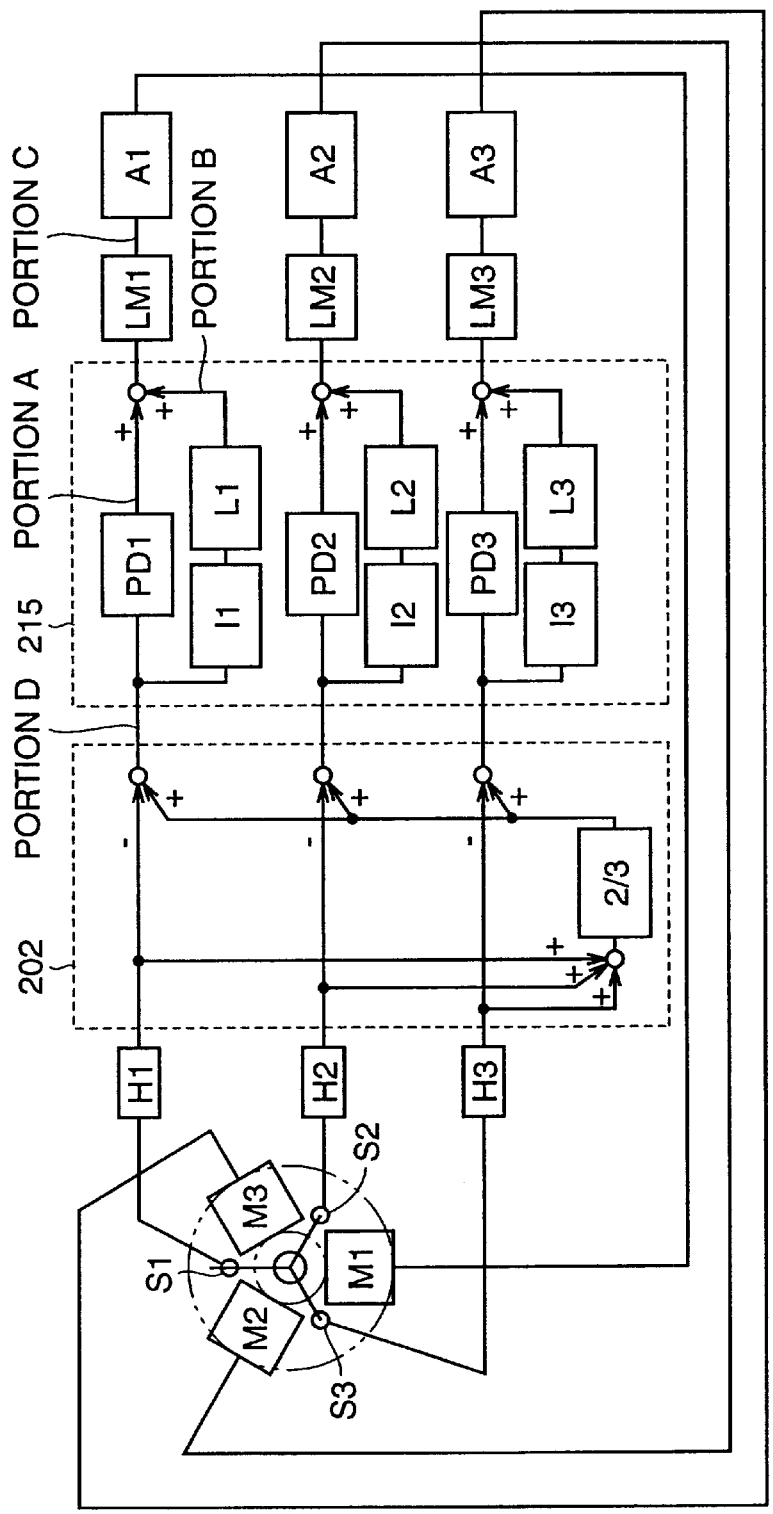
FIG. 12 is a block diagram showing the circuit controlling the maglev pump of still another embodiment of the present invention.
Figure 13A:
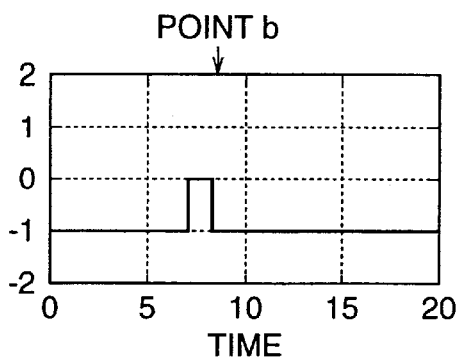
FIGS. 13A–13E represent signals of different components and the impeller's movement when a stepwise disturbance is applied in the FIG. 12 maglev pump on that side of the impeller facing the electromagnet.
Figure 13B:
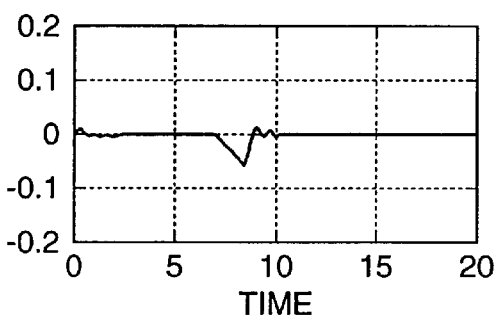
Figure 13C:
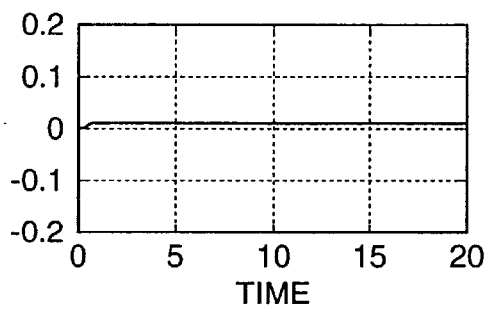
Figure 13D:
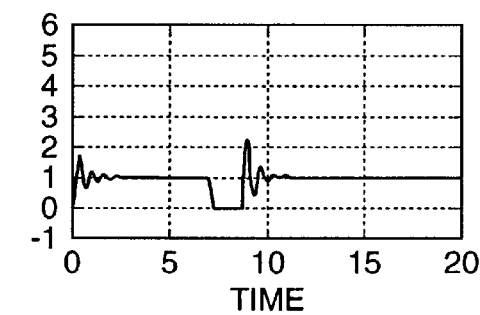
Figure 13E:
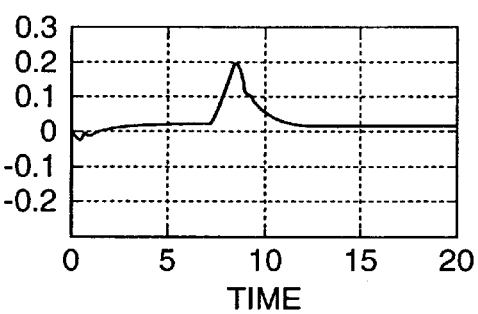

FIG. 12 is a block diagram of the control circuit of still another embodiment of the present invention. The FIG. 12 embodiment corresponds to the FIG. 9 embodiment, except that the FIG. 9 limit circuits L1–L3 are connected to follow integral circuits I1–I3. In the FIG. 12 embodiment, limit circuit L1–L3 also only pass a positive-voltage signal input and compulsorily set a negative-voltage signal to be 0V.

FIGS. 13A–13E represent a signal of each component and the impeller's movement for the FIG. 12 control circuit when a stepwise disturbance is applied on that surface of the impeller facing an electromagnet. As is apparent when the FIGS. 13A–13E are compared with FIGS. 11A–11E, providing limit circuits L1–L3 following integral circuits I1–I3, as shown in FIG. 12, has its effect smaller than providing limit circuits L1–L3 preceding integral circuits I1–I3, as shown in FIG. 9, although it can be understood that the former is significantly more effective than when the limit circuits are removed, as represented in FIGS. 11A–11E.

FIGS. 14A–14E represent a signal of each component and the impeller's movement when the FIG. 9 integral circuit is replaced by a lowpass circuit and a stepwise disturbance is applied on that surface of the impeller facing an electromagnet. As is apparent when the FIGS. 14A–14E are compared with FIGS. 10A–10E, if disturbance is applied each component has a waveform substantially unchanged and it can thus be understood that the FIG. 9 integral circuits I1–I3 may be replaced by a lowpass circuit.

Figure 15:
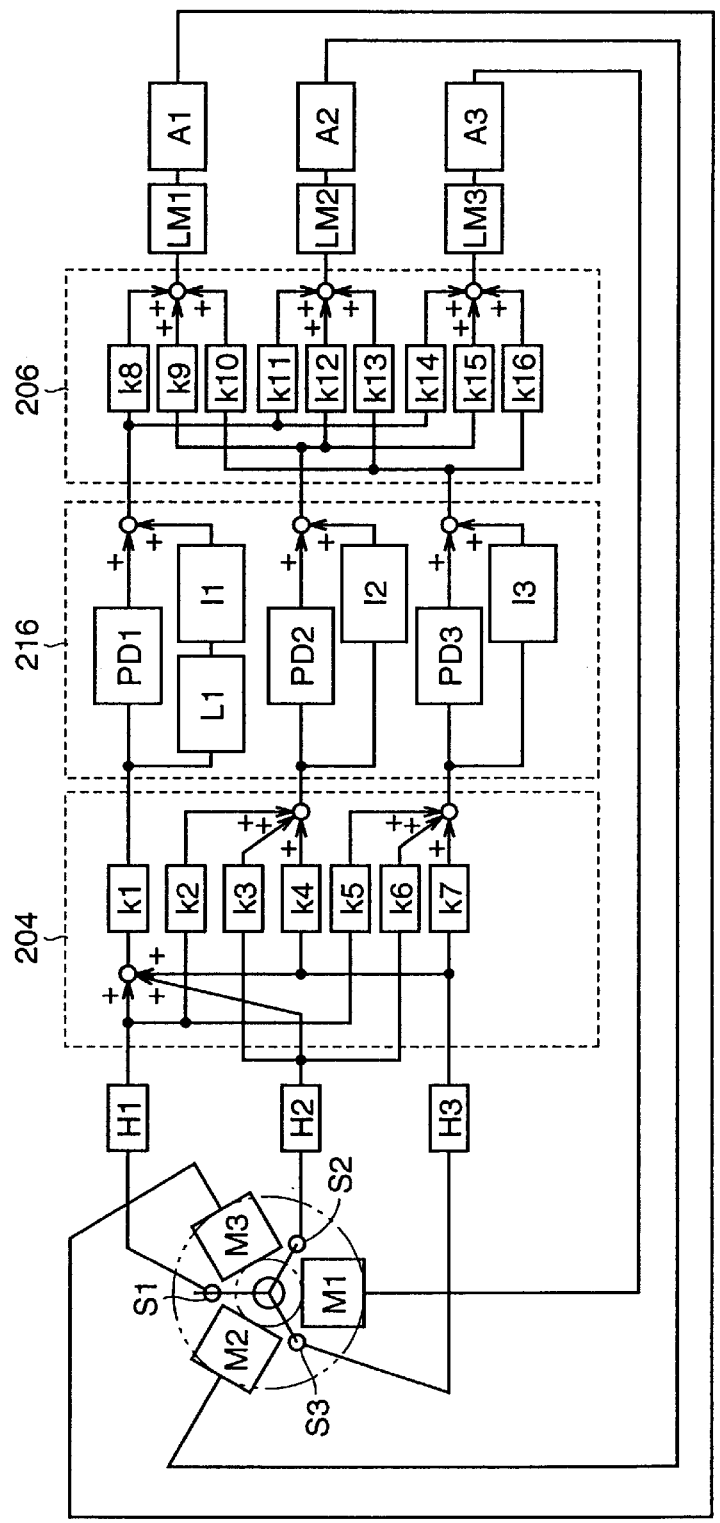
FIG. 15 is a block diagram showing an example of applying the present invention to a maglev pump provided with a phase compensation circuit for each mode of movement of an impeller controlled by a magnetic bearing.

FIG. 15 is a block diagram showing an example of the FIG. 18 conventional control circuit with an integral circuit connected to a limit circuit to follow it. In this example, for pitching and yawing movements the output value cannot be depended on to uniformly determine each electromagnet current and limit circuit L1 is connected only to a system controlling the translative movement of the impeller in the direction of its axis of rotation.

While in each embodiment described above limit circuits L1–L3 are configured to only pass a positive-voltage signal input and compulsorily set negative voltage to be 0V, it can be better in a circuit configuration that only the negative-voltage signal be passed and the positive-voltage signal be compulsorily set to be 0V.

Furthermore, limit circuits L1–L3 are not required to have a limit value set to be 0V. For example, if only passing a signal input of positive voltage while compulsorily setting a signal of negative voltage to be 0V is effective then the limit circuit may have a limit voltage shifted to have a negative value such as −0.1V. If only passing a signal input of negative voltage while compulsorily setting a signal of positive voltage to be 0V is effective then the limit circuit may have a limit voltage shifted to have a positive value such as +0.1V.

Furthermore, these circuit configurations may be configured by analog circuit or digital circuit.

Thus in the present embodiment a phase compensation circuit includes an integral circuit or a lowpass circuit having an input or an output with a limit imposed thereon. As such, if the present embodiment is used in the form of a mobile pump or it is implanted in a human body in the form of a blood pump and the entirety of the pump would move as the impeller rotates, it does not require a magnetic bearing electromagnet increased in size and can control the magnetic bearing in immediate response to disturbance applied to the pump and thus steadily support the impeller.

Although the present invention has been described and illustrated in detail, it is clearly understood that the same is by way of illustration and example only and is not to be taken by way of limitation, the spirit and scope of the present invention.

What is claimed is:

1. A magnetically levitated pump comprising:
    an impeller in a form of a disc for delivery of fluid, having one side provided with a first ferromagnetic body and the other side circumferentially provided with a second ferromagnetic body;
    an electromagnet arranged adjacent one side of said impeller to face said first ferromagnetic body to attract said impeller toward said electromagnet;
    a permanent magnet circumferentially arranged in a pump casing adjacent a pump chamber and adjacent said other side of said impeller to face said second ferromagnetic body to attract said impeller toward said permanent magnet; and
    a mechanism arranged adjacent said one side of said impeller to transmit to said impeller without contacting said impeller a force driving and thus rotating said impeller,
    wherein said impeller is magnetically levitated by controlling an electric current flowing through said electromagnet to provide in balance an attractive force provided by said permanent magnet to said second ferromagnetic body and an attractive force provided by said electromagnet to said first ferromagnetic body.

2. The pump of claim 1, wherein:
    said impeller has said one side circumferentially provided with a permanent magnet; and
    said mechanism includes a motor comprising a motor rotor having, on one side adjacent said impeller, a permanent magnet circumferentially disposed opposite said circumferentially provided permanent magnet of said impeller and a motor stator provided adjacent a side of said motor rotor opposite said one side of said motor rotor.

3. The pump of claim 2, wherein:
    said first ferromagnetic body is arranged opposite said electromagnet and said permanent magnet of said impeller is circumferentially arranged closer to an outer diameter of said impeller than an inner diameter thereof; and
    said electromagnet is arranged closer to an inner diameter of said impeller than an outer diameter thereof and said motor rotor is arranged closer to an outer diameter of said impeller than an inner diameter thereof.

4. The pump of claim 2, wherein:
    said circumferentially provided permanent magnet of said impeller is arranged closer to an inner diameter of said impeller than an outer diameter thereof and said first ferromagnetic body is arranged closer to an outer diameter of said impeller than an inner diameter thereof opposite said electromagnet; and
    said motor rotor is arranged closer to an inner diameter of said impeller than an outer diameter thereof and said electromagnet is arranged closer to an outer diameter of said impeller than an inner diameter thereof.

5. The pump of claim 1, wherein said mechanism includes a motor rotor arranged on said one side of said impeller, and a motor stator arranged opposite said motor rotor.

6. A magnetically levitated pump comprising:
    an impeller in a form of a disc for delivery of fluid, having one surface provided with a first ferromagnetic body and the other surface circumferentially provided with a second ferromagnetic body;
    an electromagnet closer to one side of said impeller to face said first ferromagnetic body to attract said impeller toward one side;
    a permanent magnet arranged closer to the other side of said impeller circumferentially to face said second ferromagnetic body to attract said impeller toward the other side; and
    a mechanism arranged closer to said one side of said impeller to transmit to said impeller without contacting said impeller a force driving and thus rotating said impeller, wherein said impeller is magnetically levitated by controlling an electric current flowing through said electromagnet to provide in balance an attractive force provided by said permanent magnet and applied to said second ferromagnetic body and an attractive force provided by said electromagnet and applied to said first ferromagnetic body, and wherein said mechanism includes a motor rotor arranged closer to one side of said impeller, and a motor stator arranged opposite said motor rotor.

7. A control circuit controlling a magnetically levitated pump, applying an electromagnetic attractive force in one direction of an impeller and at least one of a magnetic attractive force to support said impeller without contacting said impeller, said control circuit having a sensor detecting a position of the impeller and an electromagnet applying said electromagnetic attractive force to said impeller to position said impeller, comprising:

a separation circuit driven by an output of said sensor to separate a movement of said impeller into a translative movement in a direction of an axis of rotation of said impeller, a pitching movement and a yawing movement;

a phase compensation circuit including a proportional-plus-derivative circuit and one of an integral circuit and a lowpass circuit in parallel with said proportional-plus-derivative circuit for each said movement provided by said separation circuit; and a limit circuit connected to said phase compensation circuit at one of an input and an output of one of said integral circuit and said lowpass circuit controlling said translative movement.

8. The control circuit of claim 7, wherein when said impeller leans closer to said electromagnet than a position set for said impeller to be levitated, said limit circuit disconnects one of said input and said output of one of said integral circuit and said lowpass circuit controlling said translative movement.

9. The pump of claim 7, wherein said limit circuit outputs a signal representing one of positive and negative outputs of one of said input and said output of one of said integral circuit and said lowpass circuit controlling said translative movement.

10. A control circuit controlling a magnetically levitated pump, applying an electromagnetic attractive force in one direction of an impeller and at least one of a magnetic attractive force to support said impeller without contacting said impeller, said control circuit having a sensor detecting a position of the impeller and an electromagnet applying said electromagnetic attractive force to said impeller to position said impeller, comprising:

an operation circuit operative in response to an output of said sensor to perform an operation to calculate a distance between each said electromagnet and said impeller;

a phase compensation circuit including in parallel a proportional plus derivative circuit and one of an integral circuit and a lowpass circuit receiving a signal output from said operation circuit; and a limit circuit connected to one of an input and an output of one of said integral circuit and said lowpass circuit.

11. The control circuit of claim 10, wherein when said impeller leans closer to said electromagnet than a position set for said impeller to be levitated, said limit circuit disconnects one of said input and said output of one of said integral circuit and said lowpass circuit controlling said translative movement.

12. The pump of claim 10, wherein said limit circuit outputs a signal representing one of positive and negative outputs of one of said input and said output of one of said integral circuit and said lowpass circuit controlling said translative movement.

13. The pump of claim 10, for use for blood circulation.

14. A control circuit controlling a magnetically levitated pump, applying an electromagnetic attractive force in one direction of an impeller and at least one of a magnetic attractive force to support said impeller without contacting said impeller, said control circuit having a sensor detecting a position of the impeller and an electromagnet applying said electromagnetic attractive force to said impeller to position said impeller, comprising:

a separation circuit driven by an output of said sensor to separate a movement of said impeller into a translative movement in a direction of an axis of rotation of said impeller, a pitching movement and a yawing movement;

a phase compensation circuit applying proportional, derivative and integral elements for each of said translative, pitching and yawing movements to control said pitching and yawing movements;

a filter circuit extracting only a low frequency component from each movement parameter; and an addition circuit connected to an input of each said phase compensation circuit and adding an output of each said filter circuit for said pitching and yawing movements, wherein compensation is made for a gyroscopic moment introduced when said impeller is rotating.

15. The pump of claim 14, further comprising a circuit detecting a rotation speed of said impeller to alter a level of compensation for said gyroscopic moment.

16. The pump of claim 14, for use for blood circulation.

17. A control circuit controlling a magnetically levitated pump, applying an electromagnetic attractive force in one direction of an impeller and at least one of a magnetic attractive force to support said impeller without contacting said impeller, said control circuit having a plurality of sensors detecting a position of the impeller and a plurality of electromagnets applying said electromagnetic attractive force to said impeller to position said impeller, comprising:

an operation circuit operative in response to an output of said sensor to perform an operation to calculate a distance between said electromagnet and said impeller;

a phase compensation circuit controlling an electromagnetic attractive force of each of said electromagnets via proportional, derivative and integral elements receiving a signal output from said operation circuit; and;

a circuit extracting a low frequency component from a signal obtained from an operation calculating a distance between an adjacent one of said electromagnets and said impeller, and adding said low frequency component to an input of said phase compensation circuit, wherein compensation is made for a gyroscopic moment introduced when said impeller is rotating.

18. A control circuit controlling a magnetically levitated pump, applying an electromagnetic attractive force in one direction of an impeller and at least one of a magnetic attractive force to support said impeller without contacting said impeller, said control circuit having a plurality of sensors detecting a position of the impeller and a plurality of electromagnets applying said electromagnetic attractive force to said impeller to position said impeller, comprising:

an operation circuit operative in response to an output of said sensor to perform an operation to calculate a distance between said electromagnet and said impeller;

a phase compensation circuit controlling an electromagnetic attractive force of each of said electromagnets via proportional, derivative and integral elements receiving a signal output from said operation circuit; and an addition circuit adding only a signal output from a corresponding said integral element and an output of an adjacent said phase compensation circuit together, wherein compensation is made for a gyroscopic moment introduced when said impeller is rotating.

19. A magnetically levitated pump comprising:

an impeller in a form of a disc for delivery of fluid, having one side provided with a first ferromagnetic body and the other side circumferentially provided with a second ferromagnetic body;

an electromagnet arranged adjacent one side of said impeller to face said first ferromagnetic body to attract said impeller toward said electromagnet;

a third ferromagnetic body circumferentially arranged in a pump casing adjacent a pump chamber and adjacent said other side of said impeller to face said second ferromagnetic body to attract said impeller toward said third ferromagnetic body; and a mechanism arranged adjacent said one side of said impeller to transmit to said impeller without contacting said impeller a magnetic force driving and thus rotating said impeller, wherein at least either said second or third ferromagnetic body is a permanent magnet; and said impeller is magnetically levitated by controlling an electric current flowing through said electromagnet to balance an attractive force between said third ferromagnetic body and said second ferromagnetic body with an attractive force provided by said electromagnet to said first ferromagnetic body under the effect of said magnetic force.

20. The pump of claim 19, wherein:

said impeller has said one side circumferentially provided with a permanent magnet; and said mechanism includes a motor comprising a motor rotor having, on one side adjacent said impeller, a permanent magnet circumferentially disposed opposite said circumferentially provided permanent magnet of said impeller and a motor stator provided adjacent a side of said motor rotor opposite said one side of said motor rotor.

21. The pump of claim 20, wherein:

said first ferromagnetic body is arranged opposite said electromagnet and said permanent magnet of said impeller is circumferentially arranged closer to an outer diameter of said impeller than an inner diameter thereof; and said electromagnet is arranged closer to an inner diameter of said impeller than an outer diameter thereof and said motor rotor is arranged closer to an outer diameter of said impeller than an inner diameter thereof.

22. The pump of claim 20, wherein:

said circumferentially provided permanent magnet of said impeller is arranged closer to an inner diameter of said impeller than an outer diameter thereof and said first ferromagnetic body is arranged closer to an outer diameter of said impeller than an inner diameter thereof opposite said electromagnet; and said motor rotor is arranged closer to an inner diameter of said impeller than an outer diameter thereof and said electromagnet is arranged closer to an outer diameter of said impeller than an inner diameter thereof.

23. The pump of claim 19, wherein said mechanism includes a motor rotor arranged on said one side of said impeller, and a motor stator arranged opposite said motor rotor.

* * * * *